United States Patent [19]

Rosen

[11] Patent Number: 4,834,964

[45] Date of Patent: May 30, 1989

[54] USE OF CHARGED NITROXIDES AS NMR IMAGE ENHANCING AGENTS FOR CSF

[75] Inventor: Gerald M. Rosen, Chapel Hill, N.C.

[73] Assignee: M.R.I., Inc., Chapel Hill, N.C.

[21] Appl. No.: 836,867

[22] Filed: Mar. 7, 1986

[51] Int. Cl.$^4$ .................. A61K 49/00; A61B 5/05; A61B 6/00
[52] U.S. Cl. ............................................ 424/9; 424/4; 128/653; 128/654; 436/173; 436/806; 600/12
[58] Field of Search ............... 424/9, 4; 436/173, 806; 128/653, 654; 546/246; 600/12

[56] References Cited

U.S. PATENT DOCUMENTS 4,656,026  4/1987  Coffman et al. .................. 424/9

FOREIGN PATENT DOCUMENTS 0133674  3/1985  European Pat. Off. .

OTHER PUBLICATIONS

Griffeth et al., Inves. Rad., vol. 19, Nov.-Dec. 1984, pp. 553-562.
Organic Chemistry, 3rd Edition, Morrison, et al., (Eds.), 1974, pp. 752-755.
Medicinal Chemistry, 2nd Edition, Burger, A. (Ed.), 1960, p. 43.
Brasch, et al., Radiology, vol. 147, (1983), pp. 773-779.
Keana, J.F.W., Chemical Reviews, vol. 78, No. 1, (1978), pp. 37-64.
Biological Magnetic Resonance, Berliner, et al., (Eds.), Plenum Press, New York, 1982, pp. 1-11.

*Primary Examiner*—Robert J. Warden
*Assistant Examiner*—Stephen C. Wieder
*Attorney, Agent, or Firm*—Millen & White

[57] ABSTRACT

Charged, stable, organic nitroxides, e.g., charged by a quaternary ammonium or a Bronsted acid group, are useful as NMR image enhancing agents for cerebrospinal fluid.

16 Claims, No Drawings

USE OF CHARGED NITROXIDES AS NMR IMAGE ENHANCING AGENTS FOR CSF

BACKGROUND OF THE INVENTION

This invention relates to NMR image enhancing agents for cerebrospinal fluid (CSF) and their use as such.

The use of NMR imaging as a diagnostic tool is only about 15 years old. For a discussion of the history of the development of this technology, see Science 83, (1983), July/August Issue, pp 60–65. For a general explanation of the technology, see Pykett, Ian L., Scientific American, 1982, May, pp. 81–88.

Medically useful NMR images presently are generated from the resonance of hydrogen nuclei provided by water and small, hydrogen-rich molecules in the body fluids and tissues. Differences in concentration, amounts, and source of these hydrogen nuclei in different regions of the body area being examined permits the generation by computer of images of that area. Proposed and established uses of NMR images include detection of tumors and other abnormalities of the brain, breast, kidney and lung, cancers, distinguishing benign from malignant tumors, detection of necrotic tissue and ischemia, diagnosing heart attacks, heart disease, degenerative diseases, strokes and a variety of lesions, e.g., of the kidney and other organs, examination of the cranial cavity, spinal column and discs, and evaluation of the effect of treatment on known cancerous tumors.

Notwithstanding the great potential of NMR as a soft tissue imaging technique, there are a variety of situations where current NMR technology generates a less than optimum image. One example of the CSF. Therefore, there is considerable interest in NMR image-enhancing agents which, when present in an area of the body containing CSF, enhance the emitted signal by reducing the relaxation time of the CSF in the area subjected to the NMR image.

NMR imaging agents are, by definition, paramagnetic, i.e., they have an unpaired electron. Polyvalent paramagnetic metal-containing compounds, e.g., organo-gadolinium compounds, are obvious candidates as NMR image enhancing agents but may be too toxic or irritating to be viable commercial products for in vivo use in human CSF. Moreover, the gadolinium chelate reported in the literature as being tested for this use required relatively high doses (0.125–250 mmoles) and repetitive dosages to achieve acceptable enhancement of the NMR image. See Dichiro et al., Radiology 1985; 157: 373–377.

Nitroxides similarly have the theoretical potential for use commercially as in vivo NMR imaging agents because they meet several of the criteria required for all such products, e.g., prolonged storage stability at varying pH and temperature, feasible methods of preparation, good shelf life, chemical flexibility which permits structural variation to adapt to specific end-use environments, and longer spin relaxation times compared to inorganic paramagnetic ions. However, the nitroxides examined to date are not practical for such use because they are rapidly enzymatically reduced in tissues to products which do not enhance the NMR signal. See "Pharmacokinetics of Nitroxide NMR Contrast Agents," Giffeth, et al., Invest. Radiol. 19: 553–562 (1984), of which I am coauthor. Brasch, et al., in Radiology 147: 773–779 (1983), report the successful enhancement of an NMR image with "TES", a piperidine mononitroxide stable free radical. Although that compound is stated by the authors to have an in vivo half life of 38 minutes, the dose employed by them to achieve a substantial increase in intensity of signal from the renal parenhyma was 0.5 g/kg body weight by intravenous injection. Such a high dose suggest that the authors compensated for the rapid enzymatic reduction of the nitroxide by the use of such a massive dose of the nitroxide that it overwhelmed reductases in the tissue under study. I have found that unless the enzyme system is overwhelmed in this manner, the in vivo reduction of virtually all nitroxides is virtually instantaneous. Needless to say, such a procedure is contraindicated for human use. Because of the relatively low electrochemical potential, viz., about 300 mV, which is characteristic of all nitroxides having an isolated nitroxide group, the rapid enzymatic reduction and, accordingly, their limited half-life at acceptably low blood levels, have rendered nitroxides as a class poor candidates as commercially useful medical NMR image enhancing agents.

U.S. Pat. No. 3,704,235 is concerned with the preparation of tropane nitroxides. These compounds are quite toxic because they are reduced by enzymes such as FAD-containing monooxygenase to give superoxide. They are also too unstable to have a useful half-life in vivo.

U.S. Pat. No. 3,716,335 relates to the use of nitroxides as sensors of certain electron transfer reactions and is not related to the use of nitroxides as NMR contrast enhancing agents.

U.S. Pat. No. 3,702,831 relates to the use of nitroxides as a magnetometer to monitor magnetic fields. This is only remotely related in that the magnetic field set-up by the free radical interacts with an applied field. Thus, the nitroxide becomes a marker, a probe. The compound used, viz., di-tert-butylnitroxide is rapidly eliminated in vivo.

U.S. Pat. No. 4,099,918 describes the synthesis of pyrrolidinoxyl as probes to study biological systems. There is no mention in this patent of NMR enhancing activity. Nitroxides have been used for years as probes of membrane structure.

I have found that a class of nitroxides which, although like nitroxides in general have too short a half-life in blood to be useful as vascular NMR image enhancing agents, surprisingly have excellent half-lives in CSF and thus are excellent NMR image enhancing agents for CSF. This is particularly unexpected because I have found that most nitroxides have short half-lives in CSF as well as in blood.

OBJECTS OF THE INVENTION

It is an object of this invention to provide a method for producing an enhanced NMR image of a CSF-containing portion of the body of a vertebrate. Another object is the provision of novel NMR image enhancing agents for CSF. Other objects will be apparent to those skilled in the art to which this invention pertains.

SUMMARY OF THE INVENTION

In a method aspect, this invention relates to a method of enhancing the image obtained by NMR scanning of a portion surrounding the spinal cord of the body of a vertebrate, which comprises injecting into the vertebrate's cerebrospinal fluid (CSF), prior to the NMR scan of that portion of the body, in admixture with a non-toxic injectable pharmacologically acceptable aqueous vehicle, an amount of a charged, stable organic nitroxide which is neurologically acceptable and non-toxic in the amount injected, effective to reduce the relaxation time of the CSF during the scanning period sufficiently to enhance the NMR image produced by the scanning.

In a composition aspect, this invention relates to compositions adapted for injection into the CSF comprising, in admixture with a pharmaceutically acceptable aqueous carrier, an NMR imaging enhancing concentration of a charged, stable organic nitroxide.

DETAILED DESCRIPTION

The term "charged" nitroxide as used herein means the nitroxide compound possesses, in addition to the nitroxyl group, a functional group which at physiological pH possesses a charge, either positive or negative, e.g., a carboxylic acid group or a quaternary ammonium group. Preferably, the nitroxide is fully charged, i.e., it is not in equilibrium with a non-charged species. Thus, quaternary ammonium nitroxides are preferred over carboxylic acids which, in turn, are preferred over primary, secondary and tertiary amines. Of the acidic nitroxides in equilibrium with a non-changed species, preferred are those having a pKa of less than 7.4, more preferably less than 5. Of the basic nitroxides, those with a pKa closest to 7.4, e.g., less than 9, are preferred.

The term "stable" as used herein means the nitroxide molecule totally and the nitroxyl moiety especially has an acceptable half-life when stored under ambient conditions, e.g., greater than 2 years and preferably greater than 5 years and when in aqueous solution is stable at room temperature for at least 2 hours and preferably at least 8 hours.

The term "neurologically acceptable" means that the nitroxide produces no short or long term adverse neurological effects. The term "non-toxic" means that no local or systemic toxic effects are manifested in the host by the nitroxide at the dosages required to achieve NMR image enhancement.

The nitroxides which can be employed in the method of this invention are structurally quite diverse since it is their property of being charged, rather than their precise chemical structure, which determines their operability in the method of this invention. However, they do have certain structural features in common. As is well known, to be a stable free radical, both carbon atoms alpha to the nitroxyl group ordinarily must be fully substituted, i.e., they bear no hydrogen atoms unless a single hydrogen atom present thereon is prevented from interacting with the nitroxyl group, e.g., by being acidic enough to be replaceable by a sodium ion. The simplest such substituents are alkyl, preferably of 1-8 carbon atoms, e.g., $CH_3$, $C_2H_5$, propyl, 2-propyl, butyl, 2-butyl, heptyl, octyl, etc., groups although other groups, such as alkyl groups substituted by one or more of hydroxy, halo, acyloxy, or a carbocyclic or heterocyclic aryl group, e.g., phenyl or pyridyl, may be present instead. Another requirement is that the nitroxide be water soluble. Ordinarily, the group imparting the requisite charge to the nitroxide compound, e.g., a carbocyclic, sulfonic or phosphonic acid or quaternary ammonium group will impart the requisite solubility thereto. However, other solubilizing groups may also be present in the molecule, if desired.

The preferred charged nitroxides employed in the method of this invention are very water soluble, e.g., at least one μmole/ml., and preferably also have a low molecular weight, e.g., less than about 350 and more preferably less than 250, not including their associated metal or halogen ion, and are heterocyclic, preferably with only the nitroxide nitrogen atom as a hetero ring atom.

As stated above, physiologically, the nitroxides are both neurologically and physiologically non-toxic and pharmacologically substantially inactive, at least at the minimum concentration required to achieve the desired image enhancement, and are readily and rapidly biodegraded by normal body mechanisms when they migrate from the CSF. They are free of heavy metals, thereby avoiding the potential of residual mutagenic effects.

A preferred class of charged nitroxides are heterocyclic nitroxyl compounds of the formula

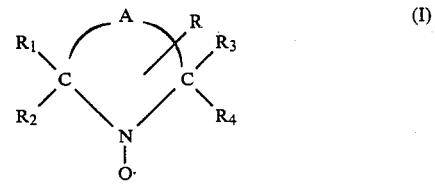

wherein
$R_1$, $R_2$, $R_3$ and $R_4$ each are alkyl of 1-4 carbon atoms;
A is alkylene or alkenylene of 2-4 carbon atoms, $-CH_2-O-CH_2-$, or $-CH_2-S-CH_2-$; and R is $-COO^-M^+$ wherein $M^+$ is ammonium, $Na^+$ or $K^+$ or R is $-N^+(Alk)_3Hal^-$ wherein Alk is alkyl of 1-8 carbon atoms or a corresponding alkyl group substituted by a free or esterified hydroxy group and $Hal^-$ is $Cl^-$, $Br^-$ or $I^-$.

Especially preferred among such compounds are those wherein $R_1$, $R_2$, $R_3$ and $R_4$ each are $CH_3$ or $C_2H_5$; those wherein A is a $-(CH_2)_2-$ or $-(CH_2)_3-$ group bearing the R group as a substituent thereon; those wherein each of $R_1$, $R_2$, $R_3$ and $R_4$ is $CH_3$ or $C_2H_5$; and those wherein R is tri-lower-alkyl-ammonium halide in which each alkyl group is $CH_3$ or $C_2H_5$ and halide is chloride, bromide or iodide.

In addition to the nitroxides employed in the examples hereinafter, other examples of NMR image enhancing agents for CSF are compounds of the formula

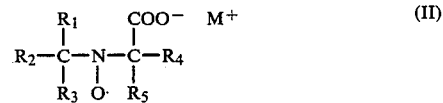

wherein $M^+$ is as defined above; $R_1$, $R_2$ and $R_3$ are the same or different and are alkyl, cycloalkyl, heterocyclic aliphatic, carbocyclic aryl or heterocyclic aryl, and preferably also are of up to 8 carbon atoms, e.g., each are methyl, ethyl, propyl, or butyl; $R_4$ and $R_5$ each are carbocyclic or heterocyclic aryl, e.g., phenyl, and $R_5$ additionally can be hydrogen, or $R_4$ and $R_5$ collectively with the alpha carbon atom form a cyclic group, for example, a cycloalkyl group, e.g., cyclopentyl or cyclohexyl. A specific example of such a compound is α-(N-t-butyl-nitroxyl)-phenylacetic acid, which is prepared by reacting 2 moles of lithio-diisopropylamine (LDA) with one mole of phenylacetic acid at −70° C. in dry THF followed by one mole of 2-methyl-2-nitrosopropane. The thus-produced hydroxylamine is oxidized with a stream of air to produce the lithium salt of the desired nitroxide, which can be converted to other salts thereof in a conventional manner by passing through a cation exchange column. This compound and others of Formula II are also useful as vascular NMR image enhancing agents.

The nitroxides of this invention are useful for enhancing the NMR imaging of the spinal canal and cisternal spaces of the cranial vault. The most common use of this type of contrast agent is assisting in the diagnosis of degenerative lumbar disease. Although NMR imaging without the aid of an imaging enhancing agent is capable of distinguishing the subarachnoid space from the discs, the use of a contrast agent of this invention allows one to gain useful information while employing $T_1$-weighted imaging with its inherent high signal-to-noise ratio, thus making NMR a much more valuable diagnostic modality in the evaluation of this pathology. Although instillation of a contrast agent of this invention still involves a lumbar puncture, because of dose thereof is very low, e.g., 0.02 mmoles in a dog, the morbidity of the examination is close to zero, which is presently not the case with metizamide injections for myelography. Additional uses of the contrast agents of this invention in the lumbar region is for the evaluation of arachnoiditis, spinal stenosis and tumors of the nerve roots as well as metastatic disease of the subarachnoid space.

In the evaluation of the thoracic area, the NMR contrast agents of this invention are invaluable in determining the extent of neoplastic and primary neoplasms. Detection of spinal cord atrophy and syrinx formation are also assisted by the contrast enhancement of the thoracic subarchnoid space achieved therewith.

To date, NMR imaging has not been as valuable in monitoring cervical degenerative disease as in the lumbar region because of the much smaller disc spaces and the lower inherent contrast of these smaller components. The NMR contrast enhancing agents of this invention eliminate this problem. Finally, tumor evaluation and syrinx visualization is improvided in the presence of these contrast enhancing agents.

The clinical usage of the contrast agents of this invention for evaluation of the cerebral subarachnoid space is also of importance. In the evaluation of the perisellar area, as well as the foramen magnum region, there are a multide of conditions for which thest contrast agents are useful. Evaluation of subarachnoid cysts, suprasellar tumors, the relationship of suprasellar tumors to surrounding brain parenchyma, Arnold-Chiari malformations, and many other diagnoses lend themselves to the use of the contrast enhancing agents of this invention.

The nitroxyl compounds of this invention are useful as NMR image enhancing agents for the CSF of all vertebrates, i.e., in addition to human beings, other mammals and non-mammals. They preferably are administered by injection as a single dose but can be administered in multiple doses or by continuous drip, e.g., in situations where NMR over several hours are contemplated. The amount administered is preferably that which achieves greater than 5%, preferably at least a 10% and more preferably at least 20% reduction in the $T_1$ relaxation time of the CSF. Ordinarily, less than 1 mmole and as little as 0.01 mmole is required to achieve an NMR image enhancing reduction in the $T_1$ relaxation time. Desirably, in humans an initial dose of at least about 0.04 mmole is employed, e.g., from about 0.05 to 2 mmoles. Generally, individual doses of about 2-100 mg, preferably about 5-50 mg, are employed.

The nitroxyl compound is ordinarily injected as a solution in a non-toxic injectable pharmacologically acceptable sterile aqueous vehicle, e.g., distilled water, physiological saline solution, CSF withdrawn from the spine of the vertebrate whose CSF-containing portion of its body is to be NMR scanned, or a mixture of the latter and either of the former. The aqueous vehicle can also contain other ingredients conventionally present in diagnostic fluids injected into the spine.

In a composition aspect, this invention relates to pharmaceutical compositions adapted for injection into the CSF comprising a charged nitroxide of this invention, e.g., those comprising an amount of a sterile solution of a concentration of about 1 to 50 mM, preferably about 10 mM, in an aqueous vehicle, of a charged organic nitroxide which is neurologically and physiologically non-toxic and effective to reduce the relaxation time of the CSF during the scanning period sufficiently to enhance the NMR image produced by the scanning. For example, the nitroxide or a solution thereof can be contained in sterile form in a conventional sealed ampoule or vial, in single or multiple dosage form, and can be at the desired injection concentration or it can be in a more concentrated form or in a dry state, so that it can be mixed with the aqueous vehicle prior to injection.

Alternatively, the nitroxide can be stored in dry form in a conventional sealed via, either alone or in admixture with a conventional solution-promoting water-soluble compound and formed into the desired injectable solution just prior to injection.

Conventional NMR scanning procedures can be employed in the method of this invention, e.g., those described by DiChino, G., et al., Radiology 1985, 157: 373-7; and Portugal, F. H., High Technology 1984, August 66-73.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLES

Preparation
4-(N,N,N-dimethylethylamino)-2,2,6,6-tetramethylpiperidinoxyl Iodide 2,2,6,6-tetramethyl-4-piperidone (I). This compound was prepared according to the method of Sandris and Ourisson, Bull Soc. Chim. Fr. 25: 345 (1985), in which 25 gms (180 mmoles) of phorone and 180 mls of ammonium hydroxide are stirred at 35° C. for 12 hrs. The solution is then cooled in an ice bath and concentrated HCl is added until the pH of the solution is 1. This solution is then saturated with NaCl and extracted with ether. The pH of the remaining liquid is raised to 10 with ammonium hydroxide followed by ether extraction. The ether solution is then dried with anhydrous sodium sulfate and evaporated to dryness, in vacuo, giving 20 gms (78%) of the desired product, B.P. 80°-85° C. at 15 mm Hg.

4-oxo-2,2,6,6-tetramethylpiperidinoxyl (II). To a solution containing 7.5 g (48.8 mmoles) of 2,2,6,6-tetramethyl-4-piperidone, 0.75 gms of sodium tungstate, and 0.75 gms of EDTA in 50 ml of water was added 10 ml of 30% hydrogen peroxide. The mixture was stirred at room temperature for 48 hrs, filtered, saturated with NaCl and the pH lowered to 3–4. This solution was extracted with ether given a red oil. Chromatographic separation using neutral alumina and methylene chloride gave 6.9 g (84%) of a red solid, M.P. 33°–35° C., E. G. Rozantsev, "Free Nitroxyl Radicals", Plenum Press, New York, pp. 213–214 (1970).

4-(N,N,N-dimethylethylamino)-2,2,6,6-tetramethylpiperidinoxyl iodide (IV). To a solution of 28.7 gms (352 mmoles) of dimethylamine:HCL dissolved in 150 ml of methanol at pH 7–8 was added 1 gm (58.8 mmoles) of (II) and 0.22 gms (35.2 mmoles) of $NaBH_3CN$ and 3A molecular sieves. The reaction was stirred at room temperature for 24 hrs, filtered and the solution was evaporated to dryness in vacuo. The remaining oil was taken up in water, saturated with NaCl, the pH lowered to 3–4, and then extracted with ether. The remaining water solution was made basic with 10% NaOH and extracted with ether, and dried over anhydrous $MgSO_4$. This solution was evaporated to dryness giving a red oil (III). The infrared spectrum of this oil no longer contained a carbonyl peak. The oil was then dissolved in ether to which excess ethyl iodide was added. Soon after the addition, a precipitate formed which was filtered and recrystallized from 95% ethanol giving (IV), M.P. 208°–210° C.

EXAMPLE 1

Stability of Nitroxide in CSF

Dogs (data is the average of 4 independent studies) under general anesthetic were injected with 2 ml of a 10 mM stock solution of 4-(N,N,N-dimethylethylamino)-2,2,6,6-tetramethylpiperidin-oxyl iodide in saline (0.9%) into the spinal cavity (3 cm below the head). At defined times, samples of CSF were removed from a catheter inserted at the point of injection. The samples were analyzed for nitroxide concentration and relaxation times. (A separate experiment determined that charged nitroxides are not bioreduced by CSF fluid. Therefore, the diminution in nitroxide concentration is attributed to active transport from the spinal cavity.) The data obtained are set forth in the table below.

PHARMACOKINETICS OF NITROXIDES IN THE CSF OF DOGS

| TIME (min) | CONCENTRATION (mM) | $T_1$ RELAXATION TIME |
|---|---|---|
| 0 |  | 3.11 |
| 5 | 3.8 | 0.904 |
| 10 | 3.3 | 1.147 |
| 20 | 2.2 | 1.751 |
| 30 | 2.0 | 1.942 |
| 45 | 1.0 | 2.439 |
| 60 | 0.72 | 2.533 |
| 75 | 0.45 | 2.546 |
| 90 | 0.22 | 2.782 |
| 105 | 0.07 | — |
| 150 | 0.03 | 2.958* |

*$T_1$ relaxation time insufficient to obtain an enhanced NMR image.

EXAMPLE 2

NMR Image Enhancement with Nitroxide

An anesthetized dog (ca. 15 kg) as described in Example 1, in a prone position with front and hind legs extended and the head supported by a pillow in the upright position, was inserted into a small animal coil of a whole-body NMR imager (General Electric 1.5 Teslar instrument). Images of two cross-sections of the cranium and four cross-sections of the spinal column at various points below the point of injection were obtained as controls. The dog was removed from the instrument, injected with the NMR image-enhancing agent as described in Example 1 and the above-described images again obtained at 7, 21, 40, 60 and 90 minutes post injection. In contradistinction to the control images, the CSF fluid in the spinal column was clearly imaged and produced a clear anatomical profile of the spinal column in each image, including the cranial sections and all of the 90 minute images. Because the loss in image enhancement is due to CSF turnover rather than decomposition of the nitroxide or passive diffusion thereof across the spinal cord, this procedure can be employed to study turnover of the CSF.

EXAMPLE 3

Follow the procedure of Example 2, employing as the charged nitroxide 0.04 millimoles of 4-(N,N-dimethyl-N-2'-hydroxyethylamino)-2,2,6,6-tetramethylpiperidinoxyl chloride. (Kornberg and McConnell, Biochemistry, Vol. 10, No. 7, 1971, pp. 1111–1120.)

EXAMPLE 4

Follow the procedure of Example 2, employing as the charged nitroxide 0.04 millimoles of the sodium salt of 4-carboxyl-2,2,6,6-tetramethylpiperidinoxyl.

EXAMPLE 5

Follow the procedure of Example 2, employing as the charged nitroxide 0.04 millimoles of a spin labeled analog of acetylcholine, namely 2-(N,N-dimethyl-N-(2,2,6,6-tetramethylpiperidinoxylamino)ethyl acetate iodide or 4-trimethylaminomethyl-4-acetoxy-2,2,6,6-tetramethylpiperidinoxyl iodide. Rosen, G. M., Abou-Donia, M. B., Synthetic Communication 1975; 5: 415–422; Rauckman, E. J., Rosen, G. M., Abou-Donia, M. B., J. Org. Chem. 1976; 41: 564; ibid, Org. Pre. Pro. Int. 1976; 8: 159–161.

EXAMPLE 6

Follow the procedure of Example 2, employing as the charged nitroxide 0.04 millimoles of the sodium salt of 1-oxyl-2,2,5,5-tetramethyl-3-pyrroline-3-carboxylic acid. (Hankovszky, H. O., Acta. Chim. Acad. Sci. Hung. 1978, 98(3), 339–48; C.A. 90: 17, 23 April (1979, p. 494) Vol. 37610b.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of enhancing the image obtained by NMR scanning of a portion surrounding the spinal cord of the body of a vertebrate, which comprises injecting into the vertebrate's cerebrospinal fluid (CSF), a composition comprising a non-toxic injectable pharmacologically acceptable aqueous vehicle and an amount of a charged, stable organic nitroxide which is neurologically acceptable and non-toxic in the amount injected, effective to reduce the T. relaxation time of the CSF and scanning the spinal cord to obtain an enhanced NMR image.

2. A method according to claim 1, wherein the vertebrate is a human being.

3. A method according to claim 2, wherein the portion of the body being scanned is a cross section of the spinal canal.

4. A method according to claim 2, wherein the amount of charged nitroxide injected is less than 0.5 millimole.

5. A method according to claim 1, wherein the nitroxide is charged by a quaternary ammonium group.

6. A method according to claim 5, wherein the quaternary ammonium group is a tri-lower-alkylammonium halide.

7. A method according to claim 1, wherein the nitroxide is charged by a carboxylic, sulfonic or phosphonic acid group.

8. A method according to claim 1, wherein the charged nitroxide is a heterocyclic nitroxyl compound of the formula

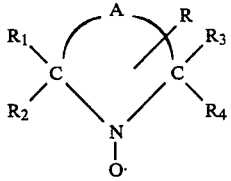

wherein
$R_1$, $R_2$, $R_3$ and $R_4$ each are alkyl of 1–4 carbon atoms;
A is alkylene or alkenylene of 2–4 carbon atoms, $-CH_2-O-CH_2-$, or $-CH_2-S-CH_2-$; and
R is $-COO^-M^+$ wherein $M^+$ is ammonium, $Na^+$ or $K^+$ or R is $-N^+(Alk)_3Hal^-$ wherein Alk is alkyl of 1–8 carbon atoms or a corresponding alkyl group substituted by a free or esterified hydroxy group and $Hal^-$ is $Cl^-$, $Br^-$ or $I^-$.

9. A method according to claim 8, wherein $R_1$, $R_2$, $R_3$ and $R_4$ are $CH_3$ or $C_2H_5$ and A is an $-(CH_2)_2-$ or $-(CH_2)_3-$ group bearing the R group.

10. A method according to claim 9, wherein R is $-COO^-M^+$ as defined therein.

11. A method according to claim 9, wherein R is $-N(Alk)_3Hal^-$ as defined therein.

12. A method according to claim 11, wherein the nitroxide is 4-(N,N-dimethyl-N-ethylamino)-2,2,6,6-tetramethylpiperidinoxyl chloride, bromide or iodide.

13. A method according to claim 11, wherein the nitroxide is 4-(N,N-dimethyl-N-ethylamino)-2,2,6,6-tetramethylpiperidinoxyl iodide.

14. A method according to claim 1, wherein the charged nitroxide is injected as a single dose.

15. A method according to claim 1, wherein the portion of the body being scanned is a cross section of the spinal canal, wherein the amount of charged nitroxide injected is less than 0.5 millimoles, wherein the charged nitrogen is administered as a single dose, and wherein the charged nitroxide is a heterocyclic nitroxyl compound of the formula

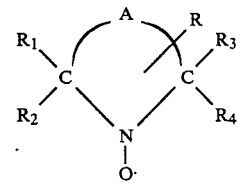

wherein
$R_1$, $R_2$, $R_3$ and $R_4$ each are alkyl of 1–4 carbon atoms;
A is alkylene or alkenylene of 2–4 carbon atoms, $-CH_2-O-CH_2-$, or $-CH_2-S-CH_2-$; and
R is $-COOM+$ wherein $M+$ is ammonium, $Na+$ or $K+$ or R is $N^+(Alk)_3Hal^-$ wherein Alk is alkyl of 1–8 carbon atoms or a corresponding alkyl group substituted by a free or esterified hydroxy group and $Hal^-$ is $Cl^-$, $Br^-$ or $I^-$.

16. A method according to claim 15, wherein the nitroxide is 4-(N,N-dimethyl-N-ethylamino)-2,2,6,6-tetramethylpiperidinoxyl chloride, bromide or iodide.

* * * * *